(12) United States Patent
Silverman et al.

(10) Patent No.: US 8,829,187 B1
(45) Date of Patent: Sep. 9, 2014

(54) CHIRAL PYRROLIDINE CORE COMPOUNDS EN ROUTE TO INHIBITORS OF NITRIC OXIDE SYNTHASE

(71) Applicant: Northwestern University, Evanston, IL (US)

(72) Inventors: Richard B. Silverman, Winnetka, IL (US); Fengtian Xue, Baton Rouge, LA (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/783,829

(22) Filed: Mar. 4, 2013

Related U.S. Application Data

(62) Division of application No. 12/781,139, filed on May 17, 2010, now Pat. No. 8,389,731.

(60) Provisional application No. 61/216,364, filed on May 15, 2009.

(51) Int. Cl.
| | |
|---|---|
| *C07D 401/06* | (2006.01) |
| *C07D 401/14* | (2006.01) |
| *C07D 405/14* | (2006.01) |
| *C07F 7/10* | (2006.01) |

(52) U.S. Cl.
CPC ............... *C07D 401/06* (2013.01); *C07F 7/10* (2013.01); *C07D 405/14* (2013.01); *C07D 401/14* (2013.01)
USPC ......................... 546/14; 546/276.4; 546/278.4

(58) Field of Classification Search
None
See application file for complete search history.

(56) References Cited

U.S. PATENT DOCUMENTS

| | | |
|---|---|---|
| 7,470,790 B2 | 12/2008 | Silverman et al. |
| 2005/0288270 A1 | 12/2005 | Allerton et al. |
| 2007/0161685 A1 | 7/2007 | Salvati et al. |
| 2008/0108814 A1 | 5/2008 | Silverman et al. |
| 2009/0111789 A1 | 4/2009 | Bartkovitz et al. |
| 2010/0029628 A1 | 2/2010 | Herold et al. |
| 2010/0166699 A1 | 7/2010 | Thompson et al. |

FOREIGN PATENT DOCUMENTS

EP 1050533 11/2000

OTHER PUBLICATIONS

Lawton et al Analogues of 2-aminopyridine-based selective inhibitors of neuronal nitric oxide synthase with increased bioavailability. Bioorganic and Medicinal Chemistry 2009, 17, 2371-2380.*
Fráter, G; Müller, U; Günther, W. The Stereoselective α-Alkylation of Chiral β-Hydroxy Esters and Some Applications Thereof. Tetrahedron, vol. 40, No. 8, pp. 1269-1277, 1984.
Marsault, E; Benakli, K; Beaubien, S; Saint-Louis, C; Déziel, R; Fraser, G. Potent macrocyclic antagonists to the motilin receptor presenting novel unnatural amino acids. Bioorganic & Medicinal Chemistry Letters 17 (2007) pp. 4187-4190.
Vyskočil, S; Jaracz, S; Smrčina, M; Štícha, M; Hanuš, V; Polášsek, M; Kočovský P. Synthesis of N-Alkylated and N-Arylated Derivatives of 2-Amino-2'-hydroxy-1,1'-binaphthyl (NOBIN) and 2,2'-Diamino-1,1'-binaphthyl and Their Application in the Enantioselective Addition of Diethylzinc to Aromatic Aldehydes. J. Org. Chem. 1998, vol. 63, No. 22, pp. 7727-7737.
Seebach, D; Aebi, J; Wasmuth, D. Org. Syn. Cioll. 1985, 7, 153.
Lawton, G.R., Ranaaivo, H.R., Chico, L.K., Ji, H., Xue, F., Martasek, P., Roman, L.J., Watterson, D.M., Silverman, R. B. Analogues of 2-aminopyridine-based selective inhibitors of neuronal nitric oxide synthase with increase bioavailability. Bioorg. & Med. Chem. Feb. 2009, 17, 2371-2380.
Xue, F., Fang, J., Lewis, W.W., Martasek, P., Roman, L.J., Watterson, D.M., Silverman, R. B. Potent and selective neuronal nitric oxide synthase inhibitors with improved cellular permeability. Bioorg. & Med. Chem. Lett. Nov. 2009, 20, 554-557.
Xue, F., Gu, W., Silverman, R.B. Concise Route to the Chiral Pyrrolidine Core of Selective Inhibitors of Neuronal Nitric Oxide. Org. Lett., vol. 11, No. 22, 2009, pp. 5194-5197. Published on Web Oct. 27, 2009.

* cited by examiner

*Primary Examiner* — Michael Barker
*Assistant Examiner* — Po-Chih Chen
(74) *Attorney, Agent, or Firm* — Reinhart Boerner Van Deuren s.c.

(57) ABSTRACT

Diastereomeric pyrrolidine compounds and methods of preparation, as can be used en route to the preparation of a range of nitric oxide synthase inhibitors.

24 Claims, 1 Drawing Sheet

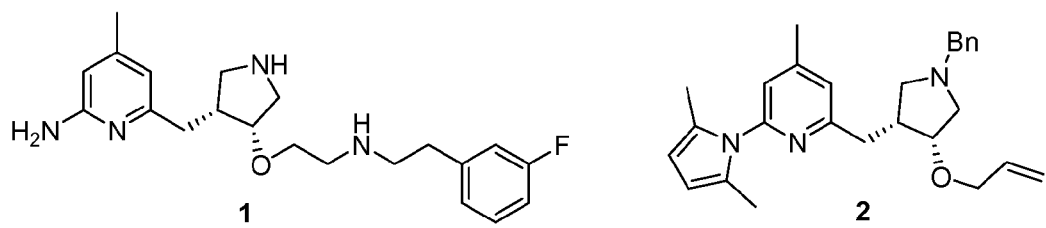
(Prior Art)

CHIRAL PYRROLIDINE CORE COMPOUNDS EN ROUTE TO INHIBITORS OF NITRIC OXIDE SYNTHASE

This application is a divisional of and claims priority benefit from application Ser. No. 12/781,139 filed May 17, 2010 and issued as U.S. Pat. No. 8,389,731 on Mar. 5, 2013, which claimed priority from application Ser. No. 61/216,364 filed May 15, 2009—each of which is incorporated herein by reference in its entirety.

This invention was made with government support under grant No. R01 GM049725 awarded by the National Institutes of Health. The government has certain rights in the invention.

BACKGROUND OF THE INVENTION

Selective inhibition of the neuronal isozyme of nitric oxide synthase (nNOS) has attracted significant interest as a novel strategy in developing therapeutics for the treatment of neurodegenerative diseases including Parkinson's disease, Alzheimer's disease, and Huntington's disease. Efforts to design nNOS selective inhibitors include development of a stereospecific pyrrolidine-based inhibitor (1, FIG. 1), which showed great potency ($K_i$=5 nM) and extremely high selectivity for nNOS over closely related isoforms, endothelial NOS (eNOS, 3800 fold) and inducible NOS (iNOS, 1200 fold). Animal tests demonstrated that 1 could lead to a remarkable reduction in neurological damage to rabbit fetuses under hypoxic conditions, making 1 a strong candidate as a new drug for the treatment of neurodegenerative diseases.

Despite these and other discoveries, current and future research related to 1 is somewhat hindered by a complicated synthesis. In particular, the chiral pyrrolidine intermediate compound 2 (FIG. 1), achieved by a seven-step procedure of the prior art, is disadvantaged by expensive starting material(s), difficult chromatographic purification(s), and low overall yield (<2%). Moreover, utilization of racemic starting materials requires extra chiral resolution step(s) using either HPLC or chiral auxiliaries, which dramatically reduce the yield and efficiency. Therefore, the development of an efficient route to chiral core compound 2 remains an ongoing concern, the absence of which will continue to impede future investigations of inhibitor 1.

SUMMARY OF THE INVENTION

In light of the foregoing, it is an object of the present invention to provide a diastereoselective synthesis of pyrrolidine core compounds, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally in all its respects, to every aspect of this invention. As such, the following objects can be viewed in the alternative with respect to any one aspect of this invention.

It can be an object of the present invention to provide a cost-effective, efficient route to chiral pyrrolidine compounds of the sort described above and illustrated elsewhere herein.

It can be another object of the present invention to provide such compounds without use of racemic starting materials and/or difficult resolutions.

It can be another object of the present invention, alone or in conjunction with one or more of the preceding objectives, to provide a synthetic approach to a diastereomeric pyrrolidine core compound, en route to a range of NOS inhibitor compounds, including selective nNOS inhibitor compounds.

Other objects, features, benefits and advantages of the present invention will be apparent from this summary and the following descriptions of certain embodiments, and will be readily apparent to those skilled in the art of organic synthesis. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a method of preparing a chiral pyrrolidine core compound. Such a method can comprise providing a dialkyl (R)-(+)-malate or a dialkyl (S)-(−)-malate; diastereoselective alkylation of such a malate with a haloalkylheterocyclic compound to provide a corresponding alkyl-substituted malate; reduction of one ester group to provide a half-ester half-aldehyde intermediate; reductive amination of the aldehyde group of such an intermediate; reduction of the ester group of such an intermediate, to provide an alcohol; and derivatization of the alcohol moiety and subsequent intramolecular cyclization, to provide a pyrrolidine core compound. Optionally, such an alkyl-substituted malate can undergo allylation. In certain such embodiments, subsequent oxidation and reductive amination with an ethanamine can provide a corresponding NOS inhibitor compound.

In certain non-limiting embodiments, such a method can utilize an (R)-stereoisomer as a chiral starting material. An (S)-stereoisomer can be used in certain other embodiments. Regardless, various dialkyl malate starting materials are available, either commercially or by synthetic procedures well known to those skilled in the art. In particular, diisopropyl and dimethyl malate stereoisomers can be used with good effect. Likewise, with respect to an alkylheterocyclic starting material, a pyridine compound (e.g., without limitation, a haloalkylpyridine compound) can be substituted as would be understood by those skilled in the art, such substitution limited only by subsequent malate alkylation, as illustrated below. In certain non-limiting embodiments, such a heterocyclic and/or pyridine compound can comprise an amino group or a protected amino group (e.g., without limitation, with 2,5-hexanedione, to provide the corresponding 2,5-dimethylpyrrole protecting group). Regardless, in certain embodiments hexamethyl disilazide can be employed to effect alkylation, but various other bases can be utilized as would be understood by those skilled in the art. In certain such embodiments, reducing the amount of a 2-bromomethylpyridine starting material to less than stoichiometric can be used to improve yield of the resulting alkylation product.

Regardless, ester and subsequent aldehyde reduction can be achieved using various synthetic techniques understood by those skilled in the art. While the use of certain reagents is illustrated, various other reagents can be utilized, such reagents limited only by subsequent chemistry and modification of the sort described herein. For instance, without limitation, while reductive amination is illustrated using benzylamine, various other substituted amines can be employed, such compounds limited only by production of the corresponding pyrrolidine core compound, deprotection and/or subsequent chemistry thereon. Likewise, while certain embodiments provide mesylation and subsequent intramolecular cyclization, it would be known to those skilled in the art that various other alcohol derivatives can be utilized under appropriate reaction conditions to achieve similar or comparable effect.

In part, the present invention can also be directed to a method of using diastereoselective alkylation to provide a diastereomeric pyrrolidine core compound. Such a method can comprise providing a Frater-Seebach diastereoselective alkylation product of a dialkyl (R)-(+)-malate or a dialkyl (S)-(−)-malate and, for instance, a bromomethylpyridine starting material; reduction of an ester group of such an alkylation product, to provide a half-ester half-aldehyde intermediate; reductive amination of the aldehyde group of such an intermediate and reduction of the ester group of such an intermediate; and derivatization and subsequent intramolecular cyclization, to provide a corresponding, diastereomeric pyrrolidine core compound.

In certain non-limiting embodiments, such an alkylation product can be allylated, as illustrated below. In various other embodiments, the hydroxy group of such a malate starting material can be protected or otherwise derivatized, as would be understood by those skilled in the art, such protection or derivatization limited only by subsequent reaction or modification of the resulting pyrrolidine core compound en route to a specific NOS inhibitor. Regardless, in various other embodiments, with reductive amination of such a half-ester half-aldehyde intermediate, subsequent ester reduction can be achieved without intermediate isolation or purification.

Accordingly, the present invention can be directed to a compound of a formula

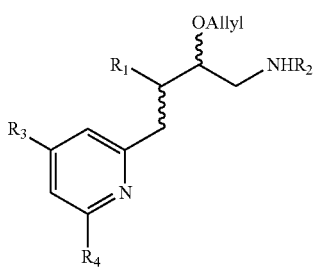

wherein $R_1$ can be selected from $C(O)OR'_1$, $CH_2OH$ and $CH_2SO_3CH_3$ moieties, where $R'_1$ can be selected from the $C_1$— about $C_6$ alkyl and $C_1$— about $C_6$ substituted alkyl moieties; $R_2$ can be selected from $C_1$— about $C_6$ alkyl and $C_1$— about $C_6$ substituted alkyl moieties; $R_3$ can be selected from H and alkyl moieties; and $R_4$ can be selected from H, amino and protected amino moieties, and salts, hydrates and/or solvates of such a compound. In certain non-limiting embodiments, $R_3$ can be an alkyl moiety, and $R_4$ can independently be a 2,5-dimethylpyrrol-1-yl moiety. When present as a salt, such a compound can be either partially or fully protonated. In certain such embodiments, a counter ion can be a conjugate base of a protic acid. Regardless, such a compound can be selected from (2S,3R) and (2R,3R) diastereomers and a mixture thereof.

In certain such embodiments, $R_2$ can be a benzyl moiety. Optionally, $R_1$ can be a $CH_2SO_3CH_3$ moiety; that is, such a compound can be mesylated to promote intramolecular cyclization. The allyl moiety of the resulting pyrrolidine compound can be oxidized to an aldehyde group, then reductively aminated with an ethanamine, such as 2-phenylethanamine, en route to a corresponding NOS inhibitor compound of the sort described in co-pending application Ser. No. 12/693,196 filed Jan. 25, 2010, the entirety of which is incorporated herein by reference.

More broadly, the present invention can be directed to the preparation of a range of chiral pyrrolidine core compounds.

Such a method can comprise providing a diastereoselective alkylation product of a chiral dialkyl malate and a haloalkyl-substituted heterocycle starting material. Subsequent steps of such a method can be as described above or illustrated elsewhere, herein. While the present invention can be illustrated in the context of a 4-methylpyridine moiety conjugated with a pyrrolidine core, it will be understood by those skilled in the art that conjugation via malate alkylation can be achieved with various other haloalkyl-pyridine and other haloalkylheterocyclic moieties. For example, without limitation, various other heterocyclic moieties including but not limited to substituted and unsubstituted thiazine, oxazine, pyrazine, oxazole and imidazole moieties—regardless of the presence or protection of an amino substituent—are described in U.S. Pat. No. 7,470,790 issued Dec. 30, 2008 and co-pending application Ser. No. 11/906,283 filed Oct. 1, 2007, in the context of substructure I as discussed more fully therein, each of which is incorporated herein by reference in its entirety. The corresponding chiral pyrrolidine core compounds can be prepared using synthetic techniques of the sort described herein or straight forward modifications thereof, as would be understood by those skilled in the art and made aware of this invention. Such heterocycle-conjugated compounds, analogous to core compound 2, can be used en route to NOS inhibitors, including selective nNOS inhibitors, of the sort described in the aforementioned incorporated references.

BRIEF DESCRIPTION OF THE DRAWINGS

FIG. 1 provides structures of an NOS inhibitor compounds of the prior art and an intermediate en route thereto.

DETAILED DESCRIPTION OF CERTAIN EMBODIMENTS

Certain embodiments of this invention illustrate the development of a concise stereospecific synthesis of 2. An initial plan was to use a disubstitution reaction on dimesylate 3 with benzylamine (Scheme 1). Dimesylated compound 3 could be derived from dialkyl malate (4) using a sequential allylation—reduction procedure. Stereospecific compound 4 could be achieved by the diastereoselective alkylation protocol developed by Frater et al. and Seebach et al. using dialkyl (R)-(+)-malate (5) and 2-(bromomethyl)-6-(2,5-dimethyl-1H-pyrrol-1-yl)-4-methylpyridine (6) as starting materials. (See, Frater, G.; Müller, U.; Günther, W. Tetrahedron 1984, 40, 1269; and Seebach, D.; Aebi, J.; Wasmuth, D. Org. Syn. Coll. 1985, 7, 153.)

Scheme 1. General Plan for the Synthesis of 2

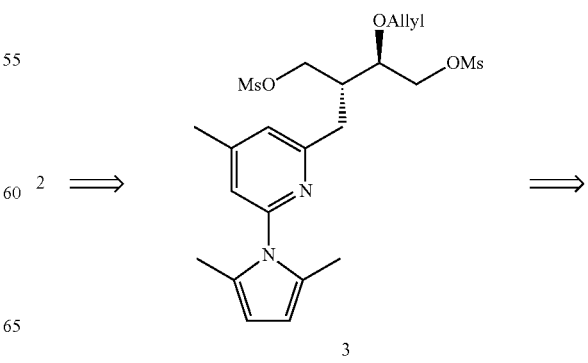

3

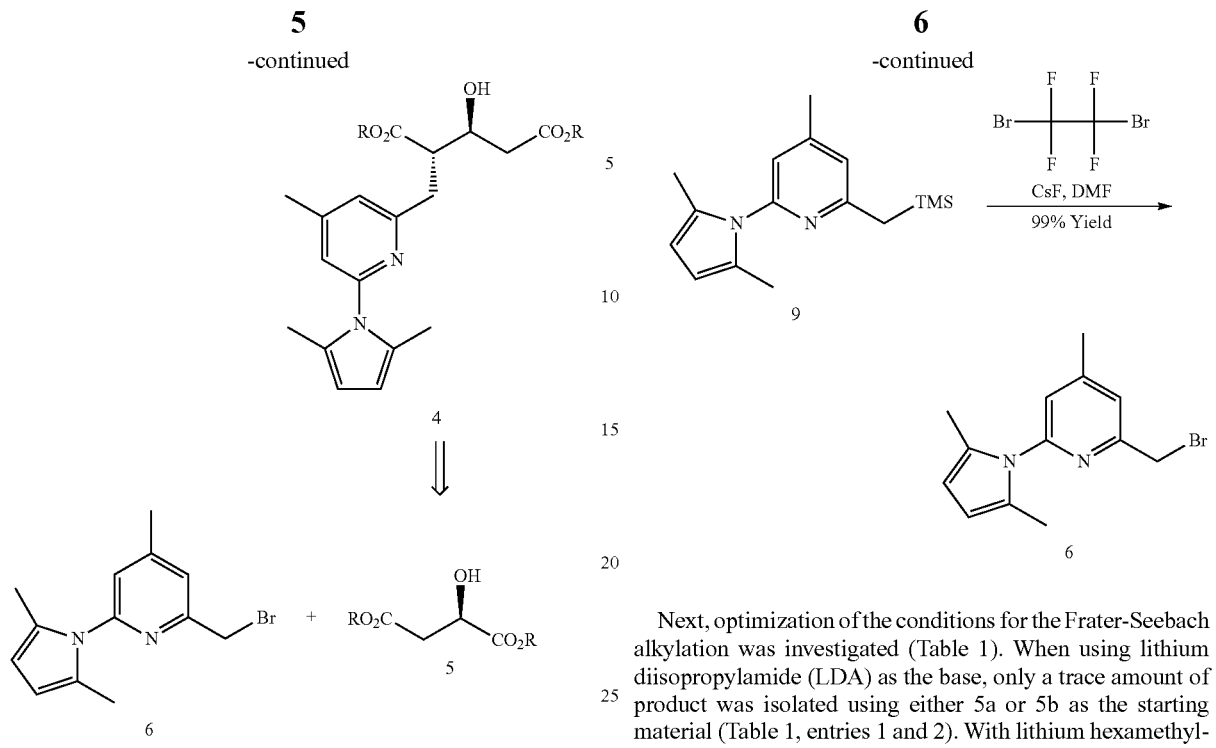

The synthesis of 6 began with 2-aminopyridine (7, Scheme 2). The amino functional group of 7 was protected using 2,5-hexanedione in the presence of p-toluenesulfonic acid (p-TsOH) to give 8 in high yields. The 2,5-dimethylpyrrole protecting group was selected for two reasons. First, this protecting group is known to be stable under a variety of reaction conditions and can be easily removed under mild conditions. Second, the electron-donating property of the 2,5-dimethylpyrrole group increases the chelating ability of the pyridine nitrogen to the lithium ion, which favors regioselective deprotonation of the 2-methyl group on the pyridine ring. 8 was treated with n-BuLi at 0° C., and the resulting anion was quenched with chlorotrimethylsilane (TMSCl) at the same temperature to generate 9 exclusively. Finally, 9 was allowed to react with 1,2-dibromotetrafluoroethane in the presence of CsF to provide 6 in quantitative yields.

Scheme 2. Synthesis of 6

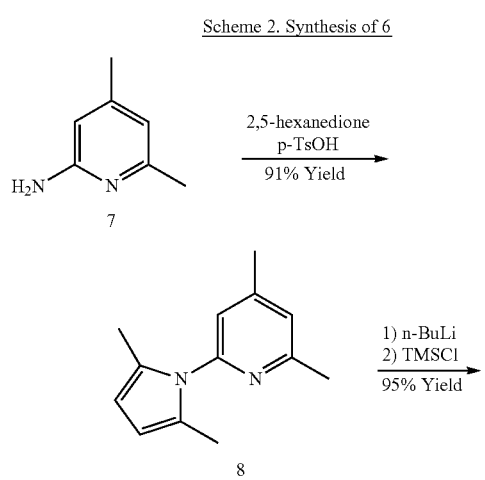

Next, optimization of the conditions for the Frater-Seebach alkylation was investigated (Table 1). When using lithium diisopropylamide (LDA) as the base, only a trace amount of product was isolated using either 5a or 5b as the starting material (Table 1, entries 1 and 2). With lithium hexamethyldisilazide (LHMDS) as the base however, products 4a and 4b could be isolated in 23% and 56% yield, respectively, with high diastereoselectivity (Table 1, entries 3 and 4). Yield was improved to 85% by changing the ratio between 5b and 6 (Table 1, entries 5 to 7).

TABLE 1

Frater-Seebach Diastereoselective Alkylation.

| entry | R | base | 6 (eq.) | yield[b] (%) | trans/cis[c] |
|---|---|---|---|---|---|
| 1 | Me | LDA | 1.0 | <2 | |
| 2 | i-Pr | LDA | 1.0 | <2 | |
| 3 | Me | LHMDS | 1.0 | 23 | 8:1 |
| 4 | i-Pr | LHMDS | 1.0 | 56 | >15:1 |
| 5 | i-Pr | LHMDS | 0.75 | 70 | >15:1 |
| 6 | i-Pr | LHMDS | 0.5 | 77 | >15:1 |
| 7 | i-Pr | LHMDS | 0.33 | 85 | >15:1 |

[a]General experimental conditions: 2 equiv of base was added to 1 equiv of 5 at −78° C., then the reaction temperature was raised to 0° C. and remained for 20 min. The reaction was cooled to −78° C. and compound 6 was added.
[b]Isolated yields.
[c]Determined by 1H NMR.

Allylation of 4b via NaH and allylbromide yielded 10, which was reduced using $LiAlH_4$ to generate diol 11 in excellent yields (Scheme 3). When 11 was submitted to a variety of mesylation conditions, however, the only products that could be detected were compounds 13 and 14, derived by intramolecular cyclizations from either the pyridinyl nitrogen atom (13) or the hydroxyloxygen atom (14), respectively.

Scheme 3. Results of Mesylation

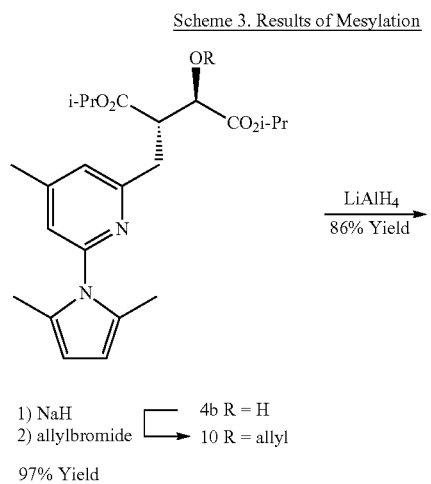

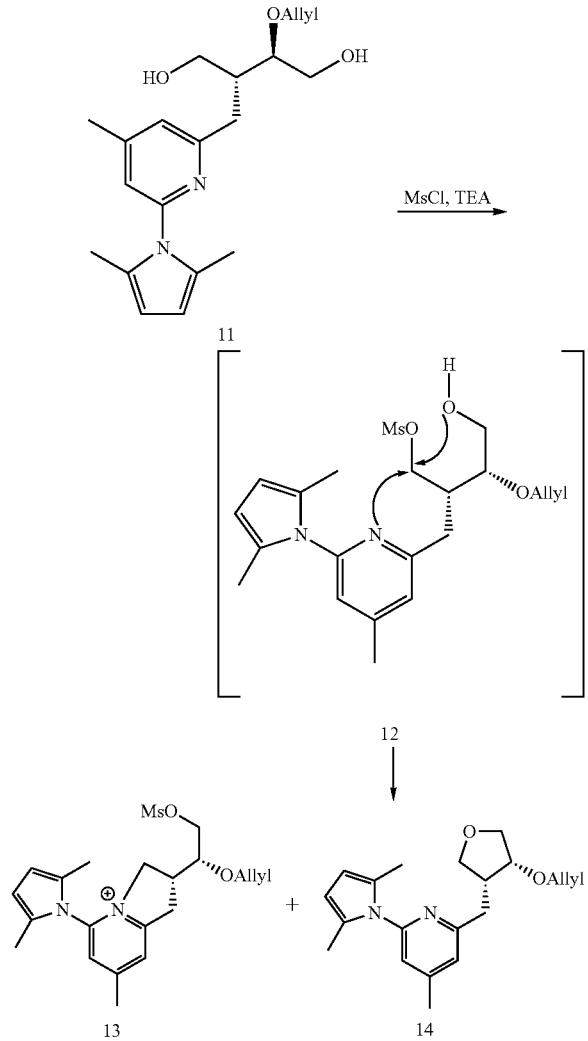

To avoid these intrinsic problems, a new synthetic route was designed around intermediate dialdehyde 15 (Scheme 4), which can undergo a single-step reductive amination reaction to provide 2. (See, Vyskočil, Š.; Jaracz, S.; Smrčina, M.; Štícha, M.; Hanuš, V.; Polášek, M.; Kočovský, P. *J. Org. Chem.* 1998, 63, 7727; and Marsault, E.; Benakli, K.; Beaubien, S.; Saint-Louis, C.; Déziel, R.; Fraser, G. *Bioorg. Med. Chem. Lett.* 2007, 17, 4187.) It was hoped that under reductive conditions, dialdehyde 15 could be generated from diisopropylester 10.

Scheme 4. Plan for the Synthesis of 2 via Dialdehyde 15

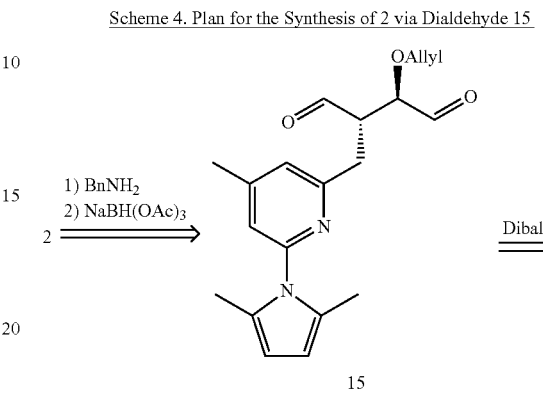

The results of the Dibal-H reduction of 10 are summarized in Table 2. When 3.5 equiv of Dibal-H were used at −78° C. for 2 h (Table 2, entry 1), three different products, aldehyde 16, alcohol 17, and semi-acetal 18, were isolated. 18 was the major product, but no dialdehyde 15 was detected. Next, fewer equiv of the reducing reagent were used. The data showed that either only aldehyde 16 (Table 2, entry 2), or 16 and 17 (Table 2, entries 3 and 4) were isolated from the reaction without any evidence of dialdehyde 15 formation. Additional reduction of aldehyde 16 using Dibal-H (1 equiv) yielded only alcohol 17, which, together with the previous Dibal-H reduction data, confirmed that dialdehyde 15 could not be generated by reduction of 10.

TABLE 2

Results of Dibal-H Reduction

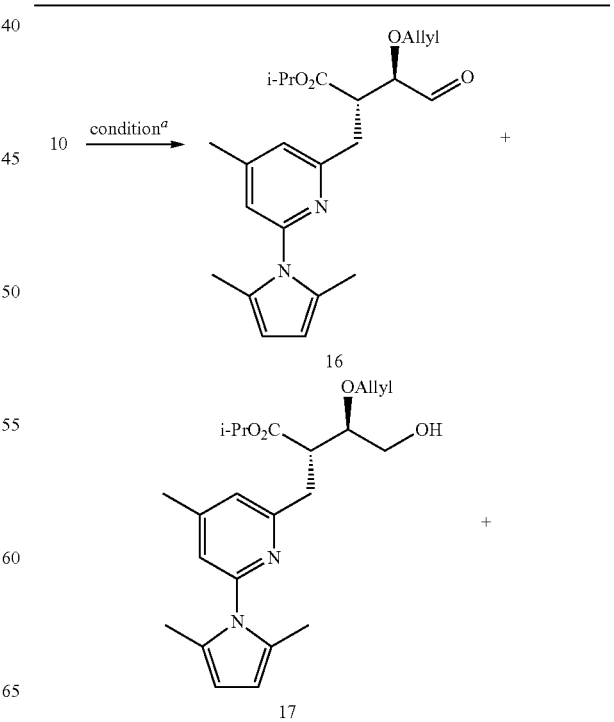

TABLE 2-continued

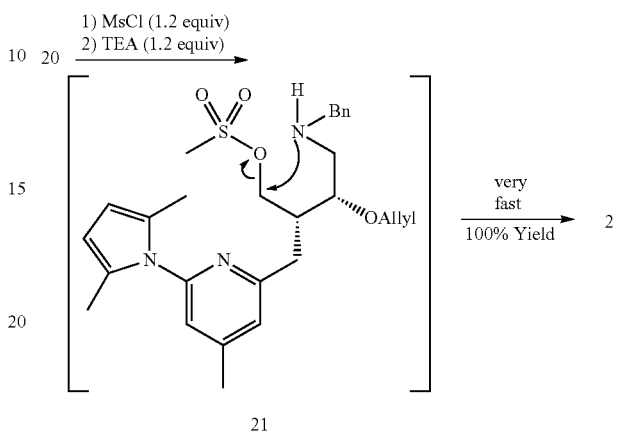

18

| entry | Dibal-H (equiv) | time (h) | yield[b] (%) | | | |
|---|---|---|---|---|---|---|
| | | | 10 | 16 | 17 | 18 |
| 1 | 3.5 | 2 | 0 | 5 | 15 | 80 |
| 2 | 2.0 | 2 | 80 | 20 | 0 | 0 |
| 3 | 2.0 | 7 | 28 | 62 | 10 | 0 |
| 4 | 1.5 | 7 | 26 | 70 | 4 | 0 |

[a]General experimental conditions: 1 equiv of 10 was added Dibal-H at −78° C.
[b]Isolated yields.

Even though dialdehyde 15 was not produced, aldehyde 16 was isolated in good yields after simple optimizations (Table 2, entry 4). Amine 20 was prepared from 16 in the hope that the additional amino group of 20 would compete with the aminopyridine nitrogen for cyclization, thus preventing the formation of 13 and yielding the desired compound 2.

Scheme 5. Synthesis of 20

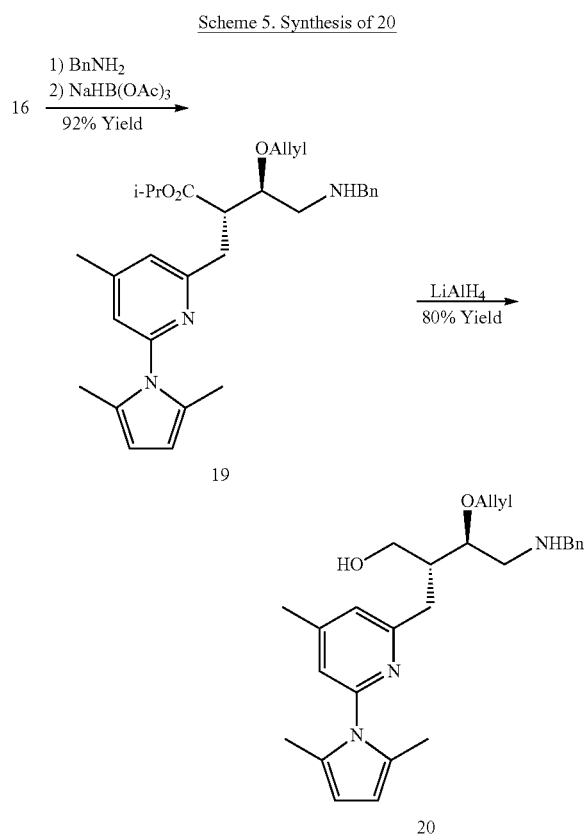

As shown in Scheme 5, reductive amination of 16 with benzylamine in the presence of NaHB(OAc)$_3$ provided amine 19 in excellent yields with complete retention of stereochemistry. Next, the isopropyl ester of 19 was reduced with LiAlH$_4$ to generate primary alcohol 20 in good yields. A one-pot procedure without purification of 19 improved the overall yield (83%).

Scheme 6.

Finally, compound 20 was treated with methylsulfonyl chloride (MsCl) in the presence of TEA. The intramolecular cyclization from the benzyl-protected amine is so fast that 2 was obtained in quantitative yields without formation of any other side products.

As shown, above, this invention provides an efficient and highly diastereoselective synthesis of the chiral pyrrolidine building block (2) for a novel nNOS inhibitor (1), employing a Frater-Seebach type alkylation and a fast intramolecular cyclization, to avoid or minimize unwanted cyclization by the pyridine nitrogen. While the preceding discussion and following examples illustrate synthesis of a (3R,4R)-diastereomer from an (R)-(+)-malate, a (3S,4S)-diastereomer can be prepared analogously from a corresponding (S)-(−)-malate.

EXAMPLES OF THE INVENTION

The following non-limiting examples and data illustrate various aspects and features relating to the methods of the present invention, including the preparation of diastereomeric pyrrolidine compounds, as are available through the synthetic methodologies described herein. In comparison with the prior art, the present methods provide results and data which are surprising, unexpected and contrary thereto. While the utility of this invention is illustrated through the use of several starting materials and substituents thereof, reactants and substituents thereof, reagents and reaction conditions which can be used therewith, it will be understood by those skilled in the art that comparable results are obtainable with various other starting materials and/or substituents (e.g., other heterocyclic and substituted heterocyclic starting materials), reactants and/or substituents, reagents and reaction conditions, as are commensurate with the scope of this invention.

General Methods.

All experiments were conducted under anhydrous conditions in an atmosphere of argon, using flame-dried apparatus and employing standard techniques in handling air-sensitive materials. All solvents were distilled and stored under an argon or nitrogen atmosphere before using. All reagents were used as received. Aqueous solutions of sodium bicarbonate, sodium chloride (brine), and ammonium chloride were saturated. Analytical thin layer chromatography was visualized by ultraviolet, ninhydrin, or phosphomolybdic acid (PMA). Flash column chromatography was carried out under a positive pressure of nitrogen. $^1$H NMR spectra were recorded on 500 MHz spectrometers. Data are presented as follows: chemical shift (in ppm on the δ scale relative to δ=0.00 ppm for the protons in TMS), integration, multiplicity (s=singlet, d=doublet, t=triplet, q=quartet, m=multiplet, br=broad), coupling constant (J/Hz). Coupling constants were taken directly from the spectra and are uncorrected. $^{13}$C NMR spectra were recorded at 125 MHz, and all chemical shift values are reported in ppm on the δ scale, with an internal reference of δ77.0 or 49.0 for CDCl$_3$ or MeOD, respectively. High-resolution mass spectra were measured on liquid chromatography/time-of-flight mass spectrometry (LC-TOF).

Preparation and Characterization of Compounds

Example 1

2-(2,5-Dimethyl-1H-pyrrol-1-yl)-4,6-dimethylpyridine (8)

To a solution of 4,6-dimethyl-2-aminopyridine (7, 12.2 g, 100 mmol) in toluene (100 mL) was added acetonylacetone (12.3 mL, 105 mmol) and p-TsOH (190 mg, 1.0 mmol). The reaction mixture was heated in a Dean-Stark apparatus under reflux for 6 h. After cooling to room temperature, the mixture was concentrated with a rotary evaporator, and the resulting brown oil was purified by flash column chromatography (EtOAc/hexanes, 1:19-1:9) to give 8 (18.2 g, 91 mmol, 91%) as a pale yellow solid: $^1$H NMR (500 MHz, CDCl$_3$) δ 2.13 (s, 6H), 2.40 (s, 3H), 2.56 (s, 3H), 5.88 (s, 2H), 6.85 (s, 1H), 7.00 (s, 1H); $^{13}$C NMR (125 MHz, CDCl$_3$) δ 13.4, 21.2, 24.4, 106.8, 119.9, 123.1, 128.6, 149.6, 151.7, 158.4; LCQ-MS (M+H$^+$) calcd for C$_{13}$H$_{17}$N$_2$ 201. found 201; LC-TOF-MS (M+H$^+$) calcd for C$_{13}$H$_{17}$N$_2$ 201.13917. found 201.13881.

Example 2

2-(2,5-Dimethyl-1H-pyrrol-1-yl)-4-methyl-6-((trimethylsilyl)methyl)pyridine (9)

To a solution of 8 (6.0 g, 30 mmol) in THF (100 mL) at 0° C. was added n-BuLi (1.6 M in hexanes, 21 mL, 33 mmol). The solution turned dark red during the addition. After stirring at the same temperature for an additional 2 h, chlorotrimethylsilane (4.2 mL, 33 mmol) was added dropwise to the reaction mixture. The reaction was warmed to room temperature and allowed to stir for an additional 1 h. The resulting bright yellow slurry was partitioned between EtOAc (200 mL) and H$_2$O (100 mL). The organic layer was washed with brine (100 mL), dried over NaSO$_4$, and concentrated. The crude product was purified by flash column chromatography (EtOAc/hexanes, 1:19-1:9) to give 9 (7.7 g, 28.5 mmol, 95%) as a pale yellow oil: $^1$H NMR (500 MHz, CDCl$_3$) δ 0.10 (s, 9H), 2.13 (s, 6H), 2.39 (s, 3H), 2.41 (s, 3H), 5.89 (s, 2H), 6.78 (s, 1H), 6.85 (s, 1H); $^{13}$C NMR (125 MHz, CDCl$_3$) δ−1.5, 13.1, 20.9, 29.8, 106.2, 118.7, 121.9, 128.3, 148.8, 151.5, 161.4; LCQ-MS (M+H$^+$) calcd for C$_{16}$H$_{25}$N$_2$Si 273. found 273; LC-TOF-MS (M+H$^+$) calcd for C$_{16}$H$_{25}$N$_2$Si 273.17870. found 273.17735.

Example 3

2-(Bromomethyl)-6-(2,5-dimethyl-1H-pyrrol-1-yl)-4-methylpyridine (6)

To a solution of 9 (5.6 g, 21 mmol) in DMF (100 mL) was added 1,2-dibromotetrafluoroethane (10 g, 42 mmol) and CsF (6.4 g, 42 mmol). The reaction was allowed to stir at room temperature for 3 h, and the resulting purple solution was concentrated and loaded directly on flash column chromatography (EtOAc/hexanes, 1:19-1:9) to give 6 (5.7 g, 20.8 mmol, 99%) as a pale yellow oil: $^1$H NMR (500 MHz, CDCl$_3$) δ 2.19 (s, 6H), 2.47 (s, 3H), 4.56 (s, 2H), 5.93 (s, 2H), 7.01 (s, 1H), 7.30 (s, 1H); $^{13}$C NMR (125 MHz, CDCl$_3$) δ 13.3, 21.1, 33.5, 107.1, 121.8, 122.9, 128.5, 150.7, 151.7, 156.3; LCQ-MS (M+H$^+$) calcd for C$_{13}$H$_{16}$BrN$_2$ 279. found 279; LC-TOF-MS (M+H$^+$) calcd for C$_{13}$H$_{16}$BrN$_2$ 279.04969. found 279.04963.

Example 4

(2S,3R)-dimethyl 2-((6-(2,5-dimethyl-1H-pyrrol-1-yl)-4-methylpyridin-2-yl)methyl)-3-hydroxysuccinate (4a)

Dimethyl ester 4a was synthesized using a similar procedure as for 4b (23%): $^1$H NMR (500 MHz, CDCl$_3$) δ 2.11 (s, 6H), 2.40 (s, 3H), 3.13-3.17 (dd, J=8.5, 14.5 Hz, 1H), 3.38-3.42 (m, 2H), 3.64 (s, 3H), 3.79-3.82 (m, 4H), 4.19 (br s, 1H), 5.89 (s, 2H), 6.89 (s, 1H), 7.09 (s, 1H); $^{13}$C NMR (125 MHz, CDCl$_3$) δ 13.4, 21.2, 35.7, 38.7, 48.0, 52.2, 53.1, 67.5, 70.6, 107.0, 120.8, 123.9, 128.7, 150.2, 151.9, 158.4, 171.3, 172.5, 174.0; LCQ-MS (M+H$^+$) calcd for C$_{19}$H$_{25}$N$_2$O$_5$ 361. found 361; LC-TOF-MS (M+H$^+$) calcd for C$_{19}$H$_{25}$N$_2$O$_5$ 361.17635. found 361.17630.

Example 5

(2S,3R)-Diisopropyl 2-((6-(2,5-dimethyl-1H-pyrrol-1-yl)-4-methylpyridin-2-yl)methyl)-3-hydroxysuccinate (4b)

To a dry flask containing THF (20 mL) at −78° C. was added fresh LHMDS (1.0 M in THF, 10 mL, 10 mmol). After 10 min, a solution of diisopropyl (R)-(+)-malate (5b, 1008 μL, 4.88 mmol) was added dropwise as a solution in THF (5 mL) through a cannula. The reaction was stirred at the same temperature for 10 min then transferred to an ice-bath (0° C.) for 30 min. The reaction was cooled to −78° C. again and 6 (1017 mg, 3.66 mmol) was added slowly (1 drop/sec) as a solution in THF (5 mL) through a cannula. The color of the reaction mixture turned light purple. The reaction was maintained at −78° C. for an additional 30 min then transferred to an ice-bath and slowly warm to room temperature. After 2 h, the reaction was quenched with NH$_4$Cl (1 mL) then partitioned between EtOAc (200 mL) and saturated NH$_4$Cl (150 mL). The inorganic layer was extracted with EtOAc (150 mL). The combined organic layer was washed by H$_2$O (100 mL), brine (100 mL), dried over Na$_2$SO$_4$, and concentrated. The crude yellow oil was purified by flash column chromatography (EtOAc/hexanes, 1:9-1:4) to give 4b (1.76 g, 2.56 mmol, 70%) as a pale yellow oil (without detection of any cis-isomer): $^1$H NMR (500 MHz, CDCl$_3$) δ 1.14-1.15 (d, J=6.5 Hz, 3H), 1.17-1.18 (d, J=6.0 Hz, 3H), 1.25-1.26 (d, J=6.5 Hz, 3H), 1.29-1.30 (d, J=6.0 Hz, 3H), 2.13 (s, 6H), 2.41 (s, 3H), 3.10-3.15 (dd, J=8.5, 14.0 Hz, 1H), 3.34-3.40 (m, 2H), 3.72-3.76 (dt, J=2.5, 8.0 Hz, 1H), 4.07-4.09 (dd, J=2.5, 7.0 Hz, 1H), 4.96-5.01 (m, 1H), 5.09-5.15 (m, 1H), 5.90 (s, 2H), 6.89 (s, 1H), 7.10 (s, 1H); $^{13}$C NMR (125 MHz, CDCl$_3$) δ 13.5, 21.2, 21.8, 21.9, 22.0, 36.1, 48.0, 68.8, 70.1, 70.6, 107.0, 120.7, 124.1, 128.7, 150.1, 158.7, 171.5, 173.4; LCQ-MS (M+H$^+$) calcd for C$_{23}$H$_{33}$N$_2$O$_5$ 417. found 417; LC-TOF-MS (M+H$^+$) calcd for C$_{23}$H$_{33}$N$_2$O$_5$ 417.23895. found 417.23834.

Example 6

(2R,3S)-Diisopropyl 2-(allyloxy)-3-((6-(2,5-dimethyl-1H-pyrrol-1-yl)-4-methylpyridin-2-yl)methyl) succinate (10)

To a solution of alcohol 4b (300 mg, 0.72 mmol) in THF (10 mL) at 0° C. was added NaH (60% in mineral oil, 35 mg, 0.87 mmol). The mixture was allowed to stir at 0° C. for an additional 30 min then allyl bromide (93 μL, 1.08 mmol) was added dropwise. The reaction was allowed to warm to room temperature and maintained for an additional 6 h. The reaction was quenched with saturated $NH_4Cl$ (1 mL) and partitioned between EtOAc (100 mL) and $H_2O$ (50 mL). The organic layer was washed with brine (50 mL) and dried over $Na_2SO_4$. The solvent was removed by rotary evaporation, the resulting brown oil was purified by flash column chromatography (EtOAc/hexanes, 1:9-1:1) to give 10 (316 mg, 0.69 mmol, 97%) as a pale yellow oil: $^1H$ NMR (500 MHz, $CDCl_3$) δ 1.07-1.09 (d, J=6.0 Hz, 3H), 1.16-1.19 (d, J=6.0 Hz, 3H), 1.25-1.35 (m, 6H), 2.13 (s, 6H), 2.39 (s, 3H), 3.01-3.05 (dd, J=5.5, 15.5 Hz, 1H), 3.20-3.25 (dd, J=9.5, 15.0 Hz, 1H), 3.67-3.68 (dd, J=3.0, 4.5 Hz, 1H), 3.89-3.94 (dd, J=7.0, 13.0 Hz, 1H), 4.02-4.03 (d, J=5.0 Hz, 1H), 4.24-4.28 (dd, J=4.5, 12.0 Hz, 1H), 4.93-4.96 (m, 1H), 4.97-5.17 (m, 1H), 5.17-5.19 (d, J=10.0 Hz, 1H), 5.25-5.29 (dd, J=1.5, 17.0 Hz, 1H), 5.80-5.95 (m, 3H), 6.86 (s, 1H), 7.02 (s, 1H); $^{13}C$ NMR (125 MHz, $CDCl_3$) δ 13.6, 21.2, 21.8, 21.9, 22.0, 22.1, 35.6, 47.2, 68.5, 68.9, 72.1, 78.1, 106.9, 118.0, 120.4, 123.7, 128.7, 134.2, 149.7, 151.8, 158.8, 170.4, 171.2; LCQ-MS $(M+H^+)$ calcd for $C_{26}H_{37}N_2O_5$ 457. found 457; LC-TOF-MS $(M+H^+)$ calcd for $C_{26}H_{37}N_2O_5$ 457.27025. found 457.26984.

Example 7

(2R,3R)-2-(Allyloxy)-3-((6-(2,5-dimethyl-1H-pyrrol-1-yl)-4-methylpyridin-2-yl)-methyl)butane-1,4-diol (11)

To a solution of 10 (300 mg, 0.70 mmol) in THF (15 mL) at 0° C. was added $LiAlH_4$ (55 mg, 1.4 mmol) in several portions. The reaction mixture was allowed to stir at 0° C. for 20 min then carefully quenched with $H_2O$ (50 μL). The solvent was removed by rotary evaporation, and the crude product was purified by flash column chromatography (EtOAc/hexanes, 1:2-1:1) to give 11 (205 mg, 0.60 mmol, 86%) as a colorless oil: $^1H$ NMR (500 MHz, $CDCl_3$) δ 2.10 (s, 6H), 2.30-2.38 (br s, 1H), 2.39 (s, 3H), 2.83-2.88 (dd, J=4.0, 13.5 Hz, 1H), 2.90-2.94 (dd, J=5.5, 14.0 Hz, 1H), 3.40-3.57 (m, 3H), 3.62-3.67 (m, 2H), 3.74-3.78 (dd, J=5.0, 11.5 Hz, 1H), 4.00-4.04 (dd, J=6.0, 12.5 Hz, 1H), 4.10-4.15 (dd, J=5.0, 13.5 Hz, 1H), 5.15-5.18 (dd, J=1.5, 11.5 Hz, 1H), 5.24-5.28 (dd, J=1.5, 17.5 Hz, 1H), 6.88 (s, 1H), 7.05 (s, 1H); $^{13}C$ NMR (125 MHz, $CDCl_3$) δ 13.3, 14.4, 21.2, 21.3, 36.0, 43.0, 60.6, 61.8, 61.9, 71.5, 77.1, 77.3, 77.6, 81.5, 106.9, 117.4, 120.9, 124.0, 128.7, 135.0, 150.5, 151.7, 160.3, 171.4; LCQ-MS $(M+H^+)$ calcd for $C_{20}H_{29}N_2O_3$ 345. found 345; LC-TOF-MS $(M+H^+)$ calcd for $C_{20}H_{29}N_2O_3$ 345.21782. found 345.21772.

Example 8

2-(((3R,4R)-4-(Allyloxy)-tetrahydrofuran-3-yl)methyl)-6-(2,5-dimethyl-1H-pyrrol-1-yl)-4-methylpyridine (13)

$^1H$ NMR (500 MHz, $CDCl_3$) δ 2.07 (s, 3H), 2.09 (s, 3H), 2.75 (s, 3H), 3.07 (s, 3H), 3.35-3.45 (m, 1H), 3.79-3.84 (dd, J=6.0, 18.0 Hz, 1H), 3.96-4.00 (dd, J=6.0, 12.5 Hz, 1H), 4.04-4.05 (d, J=5.0 Hz, 1H), 4.16-4.20 (dd, J=5.5, 12.0 Hz, 1H), 4.24-4.32 (m, 2H), 4.40-4.55 (m, 3H), 5.15 (s, 1H), 5.18 (s, 1H), 5.70-5.80 (m, 1H), 6.04 (s, 2H), 7.41 (s, 1H), 7.92 (s, 1H); $^{13}C$ NMR (125 MHz, $CDCl_3$) δ 12.5, 12.6, 22.7, 37.3, 37.7, 38.0, 39.7, 57.3, 67.8, 71.7, 110.0, 118.8, 125.5, 126.4, 129.3, 133.7, 144.4, 161.2; LCQ-MS $(M^+)$ calcd for $C_{21}H_{29}N_2O_4S$ 405. found 405; LC-TOF-MS $(M+H^+)$ calcd for $C_{20}H_{27}N_2O_2$ 405.18425. found 405.18398.

Example 9

2-(((3R,4R)-4-(Allyloxy)-tetrahydrofuran-3-yl)methyl)-6-(2,5-dimethyl-1H-pyrrol-1-yl)-4-methylpyridine (14)

$^1H$ NMR (500 MHz, $CDCl_3$) δ 2.09 (s, 6H), 2.40 (s, 3H), 2.85-2.92 (m, 2H), 3.09-3.13 (dd, J=5.5, 17.0 Hz, 1H), 3.66-3.81 (dd, J=8.0, 9.5 Hz, 1H), 3.82-3.87 (m, 2H), 3.88-3.91 (m, 3H), 4.02-4.06 (dd, J=5.5, 13.0 Hz, 1H), 5.16-5.18 (dd, J=1.5, 10.0 Hz, 1H), 5.26-5.29 (dd, J=1.5, 17.0 Hz, 1H), 5.85-5.89 (m, 3H), 6.87 (s, 1H), 7.02 (s, 1H); LCQ-MS $(M+H^+)$ calcd for $C_{20}H_{27}N_2O_2$ 327. found 327; LC-TOF-MS $(M+H^+)$ calcd for $C_{20}H_{27}N_2O_2$ 327.20725. found 327.20770.

Example 10

(2S,3R)-Isopropyl 3-(allyloxy)-2-((6-(2,5-dimethyl-1H-pyrrol-1-yl)-4-methylpyridin-2-yl)methyl)-4-oxobutanoate (16)

To a solution of diisopropyl ester 10 (140 mg, 0.31 mmol) in toluene (5 mL) at −78° C. was added dropwise a solution of Dibal-H (1.0 M in toluene, 620 μL, 0.62 mmol) along the side of the flask over a period of 15 min. The reaction was maintained at −78° C. during the addition and allowed to react at the same temperature for 7 h. To the resulting solution at −78° C., MeOH (100 μL) was added dropwise along the side of the flask to quench the reaction. The reaction mixture was warmed to −20° C. and poured directly onto a vigorously stirring Rochelle's solution (potassium sodium tartrate solution, 5 mL). The viscous solution was allowed to stir for an additional 30 min then settled down to two clear phases. The organic layer was separated, and the aqueous layer was extracted with ether (3×5 mL). The combined organic layers were dried over $Na_2SO_4$ and concentrated. The crude product was purified by flash column chromatography (EtOAc/hexanes, 1:9-1:4) to give 16 (75 mg, 0.19 mmol, 62%) as a colorless oil: $^1H$ NMR (500 MHz, $CDCl_3$) δ 1.11-1.13 (d, J=6.0, 3H), 1.16-1.18 (d, J=6.5, 3H), 2.11 (s, 6H), 2.40 (s, 3H), 3.01-3.04 (dd, J=6.5, 14.5 Hz, 1H), 3.28-3.33 (dd, J=8.0, 15.0 Hz, 1H), 3.60-3.73 (ddd, J=4.0, 7.0, 11.5 Hz, 1H), 3.85-3.86 (dd, J=1.0, 4.5 Hz, 1H), 4.03-4.06 (dd, J=6.0, 13.0 Hz, 1H), 4.21-4.25 (dd, J=6.0, 12.5 Hz, 1H), 4.96-4.98 (m, 1H), 5.19-5.22 (dd, J=1.5, 10.5 Hz, 1H), 5.24-5.28 (dd, J=2.0, 17.5 Hz, 1H), 5.86-5.91 (m, 3H), 6.88 (s, 1H), 7.03 (s, 1H), 9.75-9.77 (d, J=1.0 Hz, 1H); $^{13}C$ NMR (125 MHz, $CDCl_3$) δ 13.5, 21.2, 22.0, 35.4, 46.8, 69.1, 72.7, 83.1, 106.9, 107.0, 118.6, 120.7, 123.7, 128.7, 133.9, 149.9, 151.9, 158.5, 171.0, 202.5; LCQ-MS $(M+H^+)$ calcd for $C_{23}H_{31}N_2O_4$ 399. found 399; LC-TOF-MS $(M+H^+)$ calcd for $C_{23}H_{31}N_2O_4$ 399.22838. found 399.22859.

Example 11

(2S,3R)-Isopropyl 3-(allyloxy)-2-((6-(2,5-dimethyl-1H-pyrrol-1-yl)-4-methylpyridin-2-yl)methyl)-4-hydroxybutanoate (17)

$^1H$ NMR (500 MHz, $CDCl_3$) δ 1.10-1.30 (m, 6H), 2.10 (s, 6H), 2.40 (s, 3H), 2.87-3.20 (m, 3H), 3.40-3.50 (m, 2H), 3.80-4.20 (m, 5H), 5.10-5.40 (m, 4H), 5.80-5.96 (m, 3H), 6.88 (s, 1H), 7.03-7.05 (d, J=7.5 Hz, 1H); $^{13}$C NMR (125 MHz, CDCl$_3$) δ 13.5, 13.6, 21.2, 21.7, 22.0, 23.7, 31.6, 23.8, 33.4, 33.5, 45.0, 47.1, 49.5, 69.3, 69.5, 71.3, 71.6, 71.7, 71.9, 83.3, 84.0, 84.2, 99.6, 100.2, 101.2, 102.3, 103.7, 104.4, 106.8, 107.0, 108.3, 117.4, 117.5, 120.3, 120.4, 123.3, 123.4, 128.7, 134.1, 134.5, 134.6, 149.8, 151.9, 159.8, 160.1; LCQ-MS (M+H$^+$) calcd for C$_{23}$H$_{33}$N$_2$O$_4$ 401. found 401; LC-TOF-MS (M+H$^+$) calcd for C$_{23}$H$_{31}$N$_2$O$_4$ 401.24403. found 401.24336.

Example 12

(3S,4R)-4-(allyloxy)-3-((6-(2,5-dimethyl-1H-pyrrol-1-yl)-4-methylpyridin-2-yl)methyl)-tetrahydrofuran-2-ol (18 a mixture of two diastereomers): $^1$H NMR (500 MHz, CDCl$_3$) δ 2.14 (s, 6H), 2.40 (s, 3H), 2.85-3.00 (m, 1H), 3.10-3.20 (m, 2H), 3.70-3.90 (m, 2H), 3.91-4.07 (m, 2H), 4.08-4.22 (m, 2H), 5.10-5.34 (m, 2H), 5.40 (s, 1H), 5.80-6.00 (m, 3H), 6.83-6.95 (m, 1H), 6.96-7.03 (m, 1H); $^{13}$C NMR (125 MHz, CDCl$_3$) δ 13.5, 21.2, 21.9, 30.0, 34.1, 34.5, 40.6, 42.1, 68.2, 70.2, 71.5, 72.3, 73.6, 79.4, 83.8, 98.1, 100.7, 106.9, 107.0, 117.4, 118.2, 120.4, 120.6, 128.7, 134.0, 134.6, 149.8, 149.9, 151.9, 160.4; LCQ-MS (M+H$^+$) calcd for C$_{20}$H$_{26}$N$_2$O$_3$ 343. found 343; LC-TOF-MS (M+H$^+$) calcd for C$_{20}$H$_{26}$N$_2$O$_3$ 343.20217. found 343.20197.

Example 13

(2S,3R)-Isopropyl 3-(allyloxy)-4-(benzylamino)-2-((6-(2,5-dimethyl-1H-pyrrol-1-yl)-4-methylpyridin-2-yl)methyl)butanoate (19)

To a solution of 16 (240 mg, 0.6 mmol) in THF (5 mL) was added benzylamine (100 μL, 0.9 mmol) followed by NaHB(OAc)$_3$ (153 mg, 0.72 mmol). The reaction was allowed to stir for an additional 3 h then partitioned between EtOAc (100 mL) and brine (50 mL). The aqueous layer was extracted with EtOAc (50 mL). The combined organic layers were dried over Na$_2$SO$_4$ and concentrated. The crude product was purified by flash column chromatography (EtOAc:hexanes, 1:2-1:1) to give 19 (270 mg, 0.55 mmol, 92%) as a colorless oil: $^1$H NMR (500 MHz, CDCl$_3$) δ 0.99-1.01 (d, J=6.5 Hz, 3H), 1.09-1.11 (d, J=6.5 Hz, 3H), 2.13 (s, 6H), 2.37 (s, 3H), 2.76-2.85 (ddd, J=4.5, 5.0, 12.5, Hz, 1H), 2.98-3.08 (ddd, J=5.5, 14.0, 15.5, Hz, 1H), 3.49-3.52 (m, 1H), 3.81 (s, 2H), 3.82-3.89 (m, 1H), 4.04-4.08 (dd, J=6.0, 12.5, Hz, 1H), 4.09-4.12 ((dd, J=5.5, 13.0, Hz, 1H), 4.86-4.89 (m, 1H), 5.13-5.15 (dd, J=1.0, 10.0, Hz, 1H), 5.23-5.28 (dd, J=1.5, 17.0, Hz, 1H), 5.86-5.91 (m, 3H), 6.85 (s, 1H), 7.00 (s, 1H), 7.20-7.27 (m, 2H), 7.27-7.35 (m, 3H); $^{13}$C NMR (125 MHz, CDCl$_3$) δ 13.6, 21.2, 21.8, 21.9, 35.1, 47.6, 49.9, 54.0, 68.0, 71.4, 79.4, 106.8, 117.2, 120.3, 123.4, 127.2, 128.4, 128.6, 128.8, 134.9, 140.4, 149.5, 151.7, 159.4, 173.0; LCQ-MS (M+H$^+$) calcd for C$_{30}$H$_{40}$N$_3$O$_3$ 490. found 490; LC-TOF-MS (M+H$^+$) calcd for C$_{30}$H$_{40}$N$_3$O$_3$ 490.30697. found 490.30644.

Example 14

(2R,3R)-3-(Allyloxy)-4-(benzylamino)-2-((6-(2,5-dimethyl-1H-pyrrol-1-yl)-4-methylpyridin-2-yl)methyl)butan-1-ol (20)

To a solution of 19 (400 mg, 0.82 mmol) in THF (20 mL) at 0° C. was added LiAlH$_4$ (48 mg, 1.2 mmol) in several portions. The reaction mixture was allowed to stir at 0° C. for an additional 10 min then quenched with H$_2$O (25 μL). The solvent was removed by rotary evaporation, and the crude product was purified by flash column chromatography (EtOAc:hexanes, 2:1-4:1) to give 20 (280 mg, 0.66 mmol, 80%) as a colorless oil: $^1$H NMR (500 MHz, CDCl$_3$) δ 2.12 (s, 6H), 2.39 (s, 3H), 2.64-2.67 (dd, J=2.0, 12.0 Hz, 1H), 2.70-2.90 (m, 2H), 2.98-3.03 (dd, J=5.5, 12.5, Hz, 1H), 3.40-3.44 (dd, J=3.0, 11.5 Hz, 1H), 3.56-3.58 (dd, J=3.0, 6.0 Hz, 1H), 3.65-3.69 (dd, J=7.5, 11.5 Hz, 1H), 3.76-3.79 (d, J=13.0 Hz, 1H), 3.83-3.86 (d, J=13.0 Hz, 1H), 3.90-3.94 (dd, J=5.0, 12.5 Hz, 1H), 3.99-4.03 (dd, J=5.5, 12.5 Hz, 1H), 5.15-5.17 (dd, J=1.0, 10.5 Hz, 1H), 5.23-5.27 (dd, J=1.0, 18.5 Hz, 1H), 5.80-5.96 (m, 3H), 6.86 (s, 1H), 6.99 (s, 1H), 7.24-7.40 (m, 5H); $^{13}$C NMR (125 MHz, CDCl$_3$) δ 13.5, 21.2, 37.7, 46.4, 49.5, 54.0, 60.8, 70.9, 79.4, 98.9, 106.9, 117.2, 120.4, 123.7, 127.6, 128.6, 128.7, 128.9, 135.0, 139.2, 149.8, 151.8, 160.6; LCQ-MS (M+H$^+$) calcd for C$_{27}$H$_{36}$N$_3$O$_2$ 434. found 434; LC-TOF-MS (M+H$^+$) calcd for C$_{27}$H$_{36}$N$_3$O$_2$ 434.28075. found 434.28071.

Example 15

2-(((3R,4R)-4-(Allyloxy)-1-benzylpyrrolidin-3-yl)methyl)-6-(2,5-dimethyl-1H-pyrrol-1-yl)-4-methylpyridine (2)

To a solution of 20 (70 mg, 0.16 mmol) in CH$_2$Cl$_2$ (2.0 mL) at room temperature was added MsCl (15 μL, 0.19 mmol). After 2 min, triethylamine (34 μL, 0.24 mmol) was added dropwise as a solution in CH$_2$Cl$_2$ (340 μL). The reaction was allowed to stir for another 2 min and concentrated by rotary evaporation. The crude material was purified by flash column chromatography (EtOAc:hexanes, 2:1-4:1) to give 2 (66 mg, 0.16 mmol, 100%) as a colorless oil: $^1$H NMR (500 MHz, CDCl$_3$) δ 2.12 (s, 6H), 2.38 (s, 3H), 2.38-2.43 (m, 1H), 2.53-2.56 (dd, J=3.0, 10.0 Hz, 1H), 2.77-2.80 (dd, J=7.5, 8.0 Hz, 1H), 2.80-2.91 (m, 2H), 3.08-3.13 (m, 2H), 3.79-3.83 (dd, J=5.5, 13.0, Hz, 1H), 3.97-3.99 (br s, 2H), 5.14-5.16 (dd, J=1.0, 10.0, Hz, 1H), 5.23-5.26 (dd, J=1.0, 17.0, Hz, 1H), 5.80-5.89 (m, 1H), 5.89 (s, 2H), 6.84 (s, 1H), 7.00 (s, 1H), 7.20-7.40 (m, 5H); $^{13}$C NMR (125 MHz, CDCl$_3$) δ 13.5, 21.2, 36.2, 42.5, 58.4, 60.2, 61.0, 70.9, 79.1, 98.9, 106.8, 116.7, 120.1, 123.4, 127.1, 128.5, 128.7, 128.9, 135.2, 149.4, 151.8, 161.3; LCQ-MS (M+H$^+$) calcd for C$_{27}$H$_{34}$N$_3$O 416. found 416; LC-TOF-MS (M+H$^+$) calcd for C$_{27}$H$_{34}$N$_3$O 416.27019. found 416.26956.

While the principles of this invention have been described in connection with certain embodiments, it should be understood clearly that these descriptions are presented only by way of example and are not intended to limit, in any way, the scope of this invention. For instance, the methodologies of this invention can be applied more specifically to the synthesis of a range of pyrrolidine compounds wherein a haloalkylheterocyclic starting material is substituted with a non-heterocyclic starting material (e.g., benzyl bromide or a phenyl-substituted benzyl bromide as can be prepared according to Scheme 2) for use in the reaction of Table 1, en route to a corresponding non-heterocyclyl-substituted pyrrolidine compound. Likewise, alone or in conjunction with the preceding, the present methodologies can be modified as would be understood by those skilled in the art to provide various non-allylated compounds. For example, with reference to Scheme 3, use of benzyl bromide, a phenyl-substituted benzyl bromide or a bromomethylheterocycle compound can be used (instead of allylbromide) en route to the corresponding benzyl-, phenyl-substituted benzyl- or methylheterocyclyl-substituted pyrrolidine compound.

The invention claimed is:

1. A method of preparing a chiral pyrrolidine compound, said method comprising:
   providing a chiral dialkyl malate compound;
   diastereoselective alkylation of said malate compound with a haloalkylpyridine compound, to provide an alkylated malate compound;
   reduction of said alkylated malate compound, said reduction providing ester and aldehyde groups on said alkylated malate compound;
   reductive amination of said aldehyde group of said alkylated malate compound, wherein said reductive amination provides an amine group, and reduction of said ester group of said alkylated malate compound, wherein said ester reduction provides an alcohol group; and
   intramolecular cyclization of said alkylated malate compound with said amine group, to provide a chiral pyrrolidine compound.

2. The method of claim 1 wherein said chiral dialkyl malate compound is selected from (R)-(+)-malate and (S)-(−)-malate compounds.

3. The method of claim 2 wherein said chiral dialkyl malate compound has diisopropyl ester.

4. The method of claim 1 where said haloalkylpyridine compound is a bromomethylpyridine compound.

5. The method of claim 4 wherein said bromomethylpyridine compound is substituted with a protected amino group.

6. The method of claim 1 wherein said reductive amination is with a benzylamine.

7. The method of claim 1 wherein said alcohol group is mesylated.

8. The method of claim 1 wherein said reductive amination and said ester reduction are without ester-amine intermediate isolation.

9. The method of claim 1 comprising allylation of said alkylated malate compound.

10. The method of claim 9 wherein said allylation comprises treatment of said alkylated malate compound with hexamethyldisilazide.

11. A method of preparing a chiral pyrrolidine compound, said method comprising:
   alkylation of a chiral dialkyl malate compound with a haloalkylpyridine compound to provide an alkylated malate compound;
   allylation of said alkylated malate compound to provide an allylated and alkylated malate compound;
   reduction of said allylated and alkylated malate compound, said reduction providing ester and aldehyde groups on said allylated and alkylated malate compound;
   reductive amination of said aldehyde group of said allylated and alkylated malate compound, wherein said reductive amination provides an amine group, and reduction of said ester group of said allylated and alkylated malate compound, wherein said ester reduction provides an alcohol group; and
   mesylation of said alcohol group of said allylated and alkylated malate compound under reaction conditions to promote intramolecular cyclization of said allylated and alkylated malate compound with said amine group, to provide a diastereomeric pyrrolidine compound.

12. The method of claim 11 wherein said chiral dialkyl malate compound is selected from (R)-(+)-malate and (S)-(−)-malate compounds.

13. The method of claim 12 wherein said chiral dialkyl malate compound has diisopropyl ester.

14. The method of claim 11 where said haloalkylpyridine compound is a bromomethylpyridine compound.

15. The method of claim 14 wherein said bromomethylpyridine compound is substituted with a protected amino group.

16. The method of claim 11 wherein said reductive amination is with a benzylamine.

17. The method of claim 11 wherein said reductive amination and said ester reduction are without ester-amine intermediate isolation.

18. The method of claim 11 comprising oxidation of the allyl moiety of said diastereomeric pyrrolidine compound to provide an aldehyde group, and reductive amination of said aldehyde group with an ethanamine.

19. A method of preparing a diastereomeric pyrrolidine compound, said method comprising:
   providing an alkylated malate compound, said alkylated malate compound the diastereoselective alkylation product of a chiral dialkyl malate compound and a bromomethylpyridine compound;
   reduction of said alkylated malate compound, said reduction providing ester and aldehyde groups on said alkylated malate compound;
   reductive amination of said aldehyde group of said alkylated malate compound, wherein said reductive amination provides an amine group, and reduction of said ester group of said alkylated malate compound, wherein said ester reduction provides an alcohol group; and
   mesylation of said alcohol group on said alkylated malate compound to promote intramolecular cyclization of said alkylated malate compound with said amine group, said cyclization providing one of a (3R,4R)- and a (3S,4S)-diastereomeric pyrrolidine compound.

20. The method of claim 19 wherein said chiral dialkyl malate compound is selected from (R)-(+)-malate and (S)-(−)-malate compounds.

21. The method of claim 20 wherein said chiral dialkyl malate compound has diisopropyl ester.

22. The method of claim 19 wherein said reductive amination is with a benzylamine.

23. The method of claim 19 comprising allylation of said alkylated malate compound.

24. The method of claim 23 comprising oxidation of the allyl moiety of said diastereomeric pyrrolidine compound to provide an aldehyde group, and reductive amination of said aldehyde group with a 2-phenylethanamine.

* * * * *